(12) United States Patent
Kim et al.

(10) Patent No.: US 10,434,135 B2
(45) Date of Patent: Oct. 8, 2019

(54) PHARMACEUTICAL COMPOSITION FOR PREVENTING OR TREATING ARTHRITIS

(71) Applicants: Samsung Life Public Welfare Foundation, Seoul (KR); Korea Institute of Science and Technology, Seoul (KR)

(72) Inventors: Sang Jun Kim, Gyeonggi-do (KR); Young Mee Jung, Seoul (KR); Soo Hyun Kim, Seoul (KR)

(73) Assignees: Samsung Life Public Welfare Foundation, Seoul (KR); Korea Institute of Science and Technology, Seoul (KR)

( * ) Notice: Subject to any disclaimer, the term of this patent is extended or adjusted under 35 U.S.C. 154(b) by 0 days.

(21) Appl. No.: 15/556,963

(22) PCT Filed: Mar. 14, 2016

(86) PCT No.: PCT/KR2016/002502
§ 371 (c)(1),
(2) Date: Sep. 8, 2017

(87) PCT Pub. No.: WO2016/144146
PCT Pub. Date: Sep. 15, 2016

(65) Prior Publication Data
US 2018/0042984 A1   Feb. 15, 2018

(30) Foreign Application Priority Data
Mar. 12, 2015 (KR) .......................... 10-2015-0034227

(51) Int. Cl.
| | | |
|---|---|---|
| *A61K 35/28* | (2015.01) | |
| *A61K 38/08* | (2019.01) | |
| *A61K 38/10* | (2006.01) | |
| *A61K 38/16* | (2006.01) | |
| *A61K 47/26* | (2006.01) | |
| *A61K 9/00* | (2006.01) | |
| *A61K 9/06* | (2006.01) | |
| *A61K 38/04* | (2006.01) | |

(52) U.S. Cl.
CPC ............ *A61K 38/08* (2013.01); *A61K 9/0019* (2013.01); *A61K 35/28* (2013.01); *A61K 38/046* (2013.01); *A61K 38/10* (2013.01); *A61K 38/16* (2013.01); *A61K 9/06* (2013.01); *A61K 47/26* (2013.01)

(58) Field of Classification Search
CPC ........ A61K 35/28; A61K 38/08; A61K 38/10; A61K 38/16; A61K 47/26; A61K 38/046; A61K 9/0019; A61K 9/00; A61K 9/06
USPC .......................................... 514/1.1; 530/300
See application file for complete search history.

(56) References Cited

FOREIGN PATENT DOCUMENTS

| KR | 10-1348096 B1 | 1/2014 |
|---|---|---|
| KR | 10-1382484 B1 | 4/2014 |

OTHER PUBLICATIONS

Kim et al, "Therapeutic effects of neuropeptide substance P coupled with self-assembled peptide nanofibers on the progression of osteoarthritis in a rat model," Biomaterials, 2016, 74: 119-130. Available onlin Sep. 30, 2015.*
Rheumatoid Arthritis (RA) from Merck Manual, pp. 1-24. Accessed on Mar. 6, 2019.*
Tissue Engineering: Part A. vol. 21, No. 7 & 8, pp. 1237-1246 (Jan. 9, 2015).
PNAS. vol. 99, No. 15, pp. 9996-10001 (2002).
Biochemical and Biophysical Research Communications. vol. 453, No. 1, pp. 179-184 (2014).
Stem Cells International. vol. 2014, Article ID. 194318, pp. 1-13 (2014).
World Journal of Stem Cells. vol. 6, No. 5, pp. 629-636 (2014).
American Journal of Orthopedics. vol. 43, No. 12, pp. E282-E291 (2014).

* cited by examiner

*Primary Examiner* — Julie Ha
(74) *Attorney, Agent, or Firm* — Wood, Phillips, Katz, Clark & Mortimer (57) ABSTRACT

A pharmaceutical composition for preventing or treating arthritis, which comprises synthetic polypeptides; injections for preventing or treating arthritis; and a pharmaceutical composition for inducing differentiation of cartilage cells are described herein. Synthetic polypeptides of the present invention consisting of a polypeptide represented by SEQ ID NO: 1 and a polypeptide represented by SEQ ID NO: 2 have activity for recruiting stem cells to an arthritis region, inhibit apoptosis of cartilage cells, and exhibit anti-inflammatory activity and activity for promoting regeneration of cartilage cells. Thus, unlike a conventional arthritis treatment agent, the synthetic polypeptides can improve cartilage damage, can inhibit degenerative changes per se and can, at the same time, exhibit an effect as a stem cell treatment agent, and thereby can be usefully utilized as an arthritis prevention or treatment agent.

9 Claims, 5 Drawing Sheets
Specification includes a Sequence Listing.

Before Treatment – 2 Weeks – 4 Weeks

MICRO-CT Analysis

SEQUENCE LISTING

<160> NUMBER OF SEQ ID NOS: 13

<210> SEQ ID NO 1
<211> LENGTH: 12
<212> TYPE: PRT
<213> ORGANISM: Artificial
<220> FEATURE:
<223> OTHER INFORMATION: Self Assembling Peptide KLD12

<400> SEQUENCE: 1

Lys Leu Asp Leu Lys Leu Asp Leu Lys Leu Asp Leu
1               5                   10

<210> SEQ ID NO 2
<211> LENGTH: 11
<212> TYPE: PRT
<213> ORGANISM: Artificial
<220> FEATURE:
<223> OTHER INFORMATION: Substance P

<400> SEQUENCE: 2

Arg Pro Lys Pro Gln Gln Phe Phe Gly Leu Met
1               5                   10

<210> SEQ ID NO 3
<211> LENGTH: 23
<212> TYPE: PRT
<213> ORGANISM: Artificial
<220> FEATURE:
<223> OTHER INFORMATION: KLD12-SP

<400> SEQUENCE: 3

Lys Leu Asp Leu Lys Leu Asp Leu Lys Leu Asp Leu Arg Pro Lys Pro
1               5                   10                  15

Gln Gln Phe Phe Gly Leu Met
            20

<210> SEQ ID NO 4
<211> LENGTH: 18
<212> TYPE: DNA
<213> ORGANISM: Artificial
<220> FEATURE:
<223> OTHER INFORMATION: Col2_F

<400> SEQUENCE: 4
cccctgcagt acatgcgg                                                 18

<210> SEQ ID NO 5
<211> LENGTH: 22
<212> TYPE: DNA
<213> ORGANISM: Artificial
<220> FEATURE:
<223> OTHER INFORMATION: Col2_R

<400> SEQUENCE: 5
ctcgacgtca tgctgtctca ag                                            22

<210> SEQ ID NO 6
<211> LENGTH: 20
<212> TYPE: DNA
<213> ORGANISM: Artificial
<220> FEATURE:
<223> OTHER INFORMATION: SOX-9_F

<400> SEQUENCE: 6
ctgaagggct acgactggac                                               20

<210> SEQ ID NO 7
<211> LENGTH: 20
<212> TYPE: DNA
<213> ORGANISM: Artificial
<220> FEATURE:
<223> OTHER INFORMATION: SOX-9_R

<400> SEQUENCE: 7
tactggtctg ccagcttcct                                                  20

<210> SEQ ID NO 8
<211> LENGTH: 21
<212> TYPE: DNA
<213> ORGANISM: Artificial
<220> FEATURE:
<223> OTHER INFORMATION: IL-1_F

<400> SEQUENCE: 8
cacctctcaa gcagagcaca g                                                21

<210> SEQ ID NO 9
<211> LENGTH: 21
<212> TYPE: DNA
<213> ORGANISM: Artificial
<220> FEATURE:
<223> OTHER INFORMATION: IL-1_R

<400> SEQUENCE: 9
gggttccatg gtgaagtcaa c                                                21

<210> SEQ ID NO 10
<211> LENGTH: 20
<212> TYPE: DNA
<213> ORGANISM: Artificial
<220> FEATURE:
<223> OTHER INFORMATION: Caspase-3_F

<400> SEQUENCE: 10
aattcaaggg acgggtcatg                                                  20

<210> SEQ ID NO 11
<211> LENGTH: 20
<212> TYPE: DNA
<213> ORGANISM: Artificial
<220> FEATURE:
<223> OTHER INFORMATION: Caspase-3_R

<400> SEQUENCE: 11
gcttgtgcgc gtacagtttc                                                  20

<210> SEQ ID NO 12
<211> LENGTH: 20
<212> TYPE: DNA
<213> ORGANISM: Artificial
<220> FEATURE:
<223> OTHER INFORMATION: GAPDH_F

<400> SEQUENCE: 12
gacatgccgc ctggagaaac                                                  20

<210> SEQ ID NO 13
<211> LENGTH: 20
<212> TYPE: DNA
<213> ORGANISM: Artificial
<220> FEATURE:

```
<223> OTHER INFORMATION: GAPDH_R

<400> SEQUENCE: 13
agcccaggat gccctttagt                                                        20
```

PHARMACEUTICAL COMPOSITION FOR PREVENTING OR TREATING ARTHRITIS

TECHNICAL FIELD

The present invention relates to a pharmaceutical composition for preventing or treating arthritis, an injection for preventing or treating arthritis, and a pharmaceutical composition for inducing differentiation of chondrocytes, which comprise a synthetic polypeptide.

BACKGROUND ART

Bones support the body's soft tissues and body weight and protect the internal organs from external shocks by enclosing them. Moreover, bones are one of the important parts of the body that not only support muscles or organs but also store calcium or other essential minerals, such as phosphorus or magnesium, in the body.

There is a joint between bones that constitute the body. Joints can be classified into immovable joints with little or no mobility between two bones or cartilages that contact each other, such as skull or dental root, movable joints with many connective tissues and high mobility between two bones such as an animal's limb bones or jawbone, and amphiarthrodial joints. Joints generally refer to the movable joints, and the movable joints are classified into syndesmoses where both bones are connected only by ligaments and synovial joints. The synovial joint refers to a joint surrounded by a connective tissue capsule (articular capsule). The inside of the articular capsule secretes a lubricating fluid called synovial fluid, and many ligaments are located outside the articular capsule to strengthen the joint.

Cartilaginous tissue surrounds a joint and absorbs the force of joint movement. When the cartilaginous tissue is damaged, arthritis accompanied by swelling, fever, and pain is caused. Arthritis occurs regardless of race, and it is divided into more than 100 groups depending on the cause. The most common form is osteoarthritis, which is a degenerative joint disease that is mainly caused by aging, and others include rheumatoid arthritis and psoriatic arthritis, which are autoimmune diseases, and infectious septic arthritis. In particular, degenerative arthritis is generally a disease of the elderly, mainly caused by aging of the joints, but is also caused by a combination of various factors, such as genetic factors, nutritional imbalance, lack of exercise, excessive exercise or injury, wrong actions or attitudes that put a strain on the joints such as excessive labor, overload due to obesity, etc., and thus also occurs frequently in young people. As such, arthritis is a disease with a high incidence in a wide range of ages, but the damaged tissues are not naturally regenerated or restored, which limit social activities of patients for a long time and deteriorate the quality of life.

Traditionally, studies of autografting, allografting, and artificial bone grafting have been performed to treat arthritis; however, such treatments are known to have problems including complications such as infection, hematoma, etc. at the bone harvest site (autografting), the risks of disease transmission from donors (allografting), and no bone formation (artificial bone grafting).

Moreover, conservative therapies such as exercise therapy including weight control, diet therapy, injection therapy, and drug therapy, tissue regeneration therapies, and surgical therapies such as artificial joint replacement used in severe cases are also used for the treatment of arthritis.

However, exercise therapy has the effect of strengthening the surrounding tissues to delay additional symptoms, but does not fundamentally regenerate damaged tissues, and it is difficult to perform due to pain when the symptoms are severe.

Moreover, the injection of hyaluronic acid (HA), a lubricating component of the joint, is used to reduce the friction of damaged sites, thereby alleviating pain and preventing symptoms from worsening. Furthermore, for the purpose of alleviating inflammation and pain, aspirin, acetaminophen, or several nonsteroidal antiinflammatory drugs (NSAIDs) and steroidal drugs such as cortisone have been used. However, these drug therapies are not the fundamental treatment for repairing damaged tissues and are reported to damage the stomach, tissue, and bone due to side effects during long-term use, resulting in a need for additional validation.

If the above-mentioned conservative therapies are not effective or if severe pain persists, a surgical therapy to replace the damaged joint with an artificial joint is used; however, the life of the artificial joint is limited to about 10 years, and thus reoperation is needed if necessary. In this case, the difficulty in removal of the artificial joint fixed to the bone, the necessity to transplant a larger artificial joint, and the necessity of extensive surrounding bone tissues put restrictions on the reoperation. Due to these problems, more attention should be paid when applying the artificial joint replacement to young people.

With the recent development of artificial cell culture techniques, a method of artificially culturing and implantation of chondrocytes from multipotent stem cells or mesenchymal stem cells has been reported. However, it is not easy to obtain sufficient autologous cells, and in terms of adhesion, regeneration efficiency, and safety of transplanted cells, there are still many technical and cost problems to be solved for many patients.

With the advent of an aging society, the population of the elderly suffering from arthritis is steadily increasing, and joint diseases caused by excessive exercise, nutritional imbalance, obesity, etc. are also increasing in young people. Accordingly, there is a continuing need for new therapeutic agents applicable to various arthritic diseases; however, there has been no report of new therapeutic agents that can regenerate cartilaginous tissue damaged by arthritis, inhibit apoptosis of chondrocytes, and exhibit the effect of stem cell therapy, and thus there is still a need for developing such therapeutic agents.

DISCLOSURE

Technical Problem

The inventors of the present invention have studies synthetic polypeptides with the ability to mobilize stem cells and found that the synthetic polypeptides can effectively prevent and treat arthritis by increasing bone mineral density and inhibiting apoptosis of chondrocytes, thereby completing the present invention.

Accordingly, an object of the present invention is to provide a pharmaceutical composition for preventing or treating arthritis, an injection for preventing or treating arthritis, and a pharmaceutical composition for inducing differentiation of chondrocytes, which comprise a synthetic polypeptide.

Technical Solution

In order to achieve the above object, the present invention provides a pharmaceutical composition for preventing or treating arthritis, comprising a synthetic polypeptide consisting of a polypeptide represented by SEQ ID NO: 1 and a polypeptide represented by SEQ ID NO: 2.

Moreover, the present invention provides a pharmaceutical composition for preventing or treating arthritis, comprising a mixture of a polypeptide represented by SEQ ID NO: 1 and a polypeptide represented by SEQ ID NO: 3.

Furthermore, the present invention provides an injection for preventing or treating arthritis, comprising a synthetic polypeptide consisting of a polypeptide represented by SEQ ID NO: 1 and a polypeptide represented by SEQ ID NO: 2.

In addition, the present invention provides a pharmaceutical composition for inducing differentiation of chondrocytes, comprising a synthetic polypeptide consisting of a polypeptide represented by SEQ ID NO: 1 and a polypeptide represented by SEQ ID NO: 2.

Advantageous Effects

The synthetic polypeptide consisting of a polypeptide represented by SEQ ID NO: 1 and a polypeptide represented by SEQ ID NO: 2 of the present invention has the ability to mobilize stem cells to arthritic sites, inhibit apoptosis of chondrocytes, exhibit anti-inflammatory activity, and promote regeneration of chondrocytes. Therefore, unlike existing therapeutic agents for arthritis, the synthetic polypeptide of the present invention can ameliorate cartilage damage, inhibit degenerative changes themselves, and at the same time, exhibit the effect of a stem cell therapeutic agent, and thus it can be effectively used as a preventive or therapeutic agent for arthritis.

DESCRIPTION OF DRAWINGS

FIGS. 1A and 1B show the effect of treatment with KLD12-SP1, KLD12-SP2, KLD12-SP0.5, and KLD12-SP-MSC on the behavioral characteristics of rats in arthritis models, determined before the treatment and after 2 weeks and 4 weeks.

FIGS. 2A and 2B show the effect of treatment with KLD12-SP1, KLD12-SP2, KLD12-SP0.5, and KLD12-SP-MSC on improvement of bone mineral density.

FIGS. 3A and 3B show the effect of treatment with KLD12-SP1 and KLD12-SP-MSC on inhibition of apoptosis of chondrocytes.

FIGS. 4A, 4B and 4C show the effect of treatment with KLD12-SP1 or KLD12-SP-MSC on decreased expression of IL-1β and caspase-3 as inflammatory factors and increased expression of collagen type II and SOX-9 as chondrocyte differentiation factors.

FIGS. 5A and 5B show the comparison of Mankin's scores indicative of the degree of damaged cartilaginous tissue in arthritis rat models injected with KLD12-SP1, KLD12-SP2, KLD12-SP0.5 and KLD12-SP-MSC, observed by histological analysis after KLD12-SP treatment.

FIGS. 7A, 7B and 7C 6 and 7 show the quantified results of immunofluorescence panel of FIG. 6, indicating decreased expression of caspase-8 and TIMP-1, increased expression of collagen type II, and substance P (SP) retained in the knee joints of rats. FIG. 4C is a bar chart of expression area of TIMP-1.

MODE FOR INVENTION

The present invention provides a pharmaceutical composition for preventing or treating arthritis, comprising a synthetic polypeptide consisting of a polypeptide represented by SEQ ID NO: 1 and a polypeptide represented by SEQ ID NO: 2.

SEQ ID NO: 1 is a self-assembling polypeptide, and SEQ ID NO: 2 is substance P.

The synthetic polypeptide according to the present invention can effectively mobilize mesenchymal stem cells to arthritic sites by stem cell mobilization activity, inhibit apoptosis of chondrocytes, exhibit anti-inflammatory activity, and promote regeneration of chondrocytes. Therefore, unlike existing therapeutic agents for arthritis, it can ameliorate cartilage damage, inhibit degenerative changes themselves, and at the same time, exhibit the effect of a stem cell therapeutic agent.

The "polypeptide represented by SEQ ID NO: 1" and the "polypeptide represented by SEQ ID NO: 2" refer to linear molecules produced by amino acid residues joined by peptide bonds and may be prepared by a chemical synthesis method known in the art, particularly by a solid-phase synthesis technique (Merrifield, J. Amer. Chem. Soc. 85:2149-54(1963); Stewart, et al., Solid Phase Peptide Synthesis, 2nd. ed., Pierce Chem. Co.: Rockford, 111(1984)).

"Substance P" of the present invention is one of the mammalian tachykinins consisting of 11 amino acid sequences of RPKPQQFFGLM and refers to a substance that is excessively secreted in a damaged tissue and has the ability to induce mobilization of multipotent stem cells for wound repair. A spacer having a sequence consisting of 2 to 10 repeats of glycine (G) or glutamic acid (E) can be linked to the N-terminus of substance P and located between substance P and a self-assembling polypeptide consisting of the amino acid sequence of SEQ ID NO: 1 to produce a synthetic polypeptide.

The synthetic polypeptide consists of a polypeptide represented by SEQ ID NO: 1 and a polypeptide represented by SEQ ID NO: 2. It may include, without limitation, polypeptides that can achieve the present invention with the ability to mobilize stem cells, the ability to inhibit apoptosis of chondrocytes, the anti-inflammatory activity, the ability to promote regeneration of chondrocytes, the ability to ameliorate cartilage damage, and the ability to inhibit degenerative changes themselves, unlike existing therapeutic agents for arthritis, and may preferably be a polypeptide represented by SEQ ID NO: 3.

The polypeptide represented by SEQ ID NO: 3 consists of the polypeptide of SEQ ID NO: 1, which is self-assembling polypeptide KLD12, and substance P bound to KLD12, and is named "KLD12-SP" in the present invention.

"KLD12-SP" can be used by mixing with self-assembling polypeptide KLD12.

Accordingly, the present invention relates to a pharmaceutical composition for preventing or treating arthritis, comprising a mixture of a polypeptide represented by SEQ ID NO: 1 and a polypeptide represented by SEQ ID NO: 3.

The weight ratio of KLD12 represented by SEQ ID NO: 1 to KLD12-SP represented by SEQ ID NO: 3 may be, but not limited to, 200:1 to 200:200, preferably 200:1 to 200:30, more preferably 200:3 to 200:20, most preferably 200:3.5 to 200:15. In preferred embodiments, the present invention discloses polypeptides mixed at weight ratios of 200:7, 200:14, and 200:3.5, which are referred to as KLD12-SP1, KLD12-SP2, and KLD12-5P0.5, respectively. If the weight ratio exceeds 200:200, i.e., 1:1, the strength of hydrogel becomes closer to the liquid phase, and thus it is difficult to maintain the shape of the gel.

In the present invention, the term "arthritis" refers to chronic inflammation of tissues around joints, such as tendons, ligaments, muscles, etc., as well as joints in other organs of the body tissues around joints, and may be at least one selected from the group consisting of osteoarthritis, degenerative arthritis, osteochondritis dissecans, joint ligament damage, meniscus tear, infectious arthritis, psoriatic arthritis, ankylosing spondylitis, rheumatoid arthritis, and juvenile rheumatoid arthritis.

In particular, in the present invention, the degenerative arthritis may be idiopathic degenerative arthritis or secondary degenerative arthritis. The term "degenerative arthritis" refers to a disease accompanied by inflammation and pain caused by damaged bones and ligaments that constitute the joint due to progressive damage or degenerative changes of the cartilage that protects the joint, which is the most common arthritic disease. Among others, "idiopathic degenerative arthritis" is caused by aging, etc. without any specific cause and is also referred to as primary degenerative arthritis. The term "secondary degenerative arthritis" refers to the condition caused by trauma, disease, and deformity that can damage the articular cartilage, such as damaged articular cartilage after bacterial arthritis or tuberculosis arthritis. The polypeptide of the present invention can be applied to both idiopathic degenerative arthritis and secondary degenerative arthritis, more preferably to idiopathic arthritis accompanied by degenerative changes due to aging.

Arthritis, more preferably degenerative arthritis, which can be treated by the administration of the synthetic polypeptide of the present invention refers to arthritis that occurs in any joint of the body due to cartilage damage, etc., and may preferably be degenerative arthritis that occurs in at least one site selected from the group consisting of a knee, a finger, a jaw, a hip, and a waist, but not limited thereto.

Moreover, the synthetic polypeptide of the present invention inhibits apoptosis of chondrocytes.

The inhibition of apoptosis of chondrocytes is very significant in that it can not only promote regeneration of cartilage but also inhibit degenerative changes themselves at sites of arthritis, which can be caused by aging, such as degenerative arthritis.

Moreover, the synthetic polypeptide of the present invention has anti-inflammatory activity and promotes regeneration of chondrocytes. More specifically, the polypeptide of the present invention reduces the expression levels of inflammatory factors IL-1β and caspase-3 in chondrocytes and increases the expression of collagen type II and SOX-9 genes associated with chondrocyte regeneration.

Furthermore, the present invention relates to a composition for preventing or treating arthritis, further comprising mesenchymal stem cells.

The synthetic polypeptide of the present invention has an excellent ability to mobilize stem cells so that the stem cells can be mobilized to the injected site and actively differentiate. Therefore, the number of mesenchymal stem cells increases in the corresponding site without having to introduce stem cells into the site where the polypeptide is introduced, and thus it is possible to promote regeneration of chondrocytes by differentiation of stem cells. In order to maximize this effect, the mesenchymal stem cells may be mixed with the polypeptide and administered to the arthritic site. When administered in this manner, the mesenchymal stem cells used as a stem cell therapeutic agent can be more easily positioned and distributed in the arthritic site, thereby promoting regeneration of cartilage.

In addition to the synthetic polypeptide consisting of a polypeptide represented by SEQ ID NO: 1 and a polypeptide represented by SEQ ID NO: 2, the present invention may also include the use of therapeutic agents which are known to be useful for the treatment or prevention of arthritis in combination or in sequence and the use of known treatment methods such as exercise therapy, etc in combination.

The composition of the present invention contains a pharmaceutically acceptable carrier. Examples of the pharmaceutically acceptable carrier contained in the pharmaceutical composition of the present invention are those conventionally used in formulation and include, but not limited to, lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, saline, phosphate buffered saline (PBS), and media.

The pharmaceutical composition of the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995).

The pharmaceutical composition of the present invention may be administered orally or parenterally, preferably parenterally, most preferably intraarticularly.

Accordingly, the present invention relates to an injection for preventing or treating arthritis, comprising a synthetic polypeptide consisting of a polypeptide represented by SEQ ID NO: 1 and a polypeptide represented by SEQ ID NO: 2 or an injection for preventing or treating arthritis, comprising a mixture of a polypeptide represented by SEQ ID NO: 1 and a polypeptide represented by SEQ ID NO: 3. Most preferably, the injection is administered intraarticularly.

A suitable dose of the pharmaceutical composition of the present invention may vary depending on various factors such as formulation method, administration method, a patient's age, weight, and sex, severity of disease, diet, administration time, administration route, excretion rate and sensitivity to response.

Moreover, the present invention relates to a pharmaceutical composition for inducing differentiation of chondrocytes, comprising a synthetic polypeptide consisting of a polypeptide represented by SEQ ID NO: 1 and a polypeptide represented by SEQ ID NO: 2.

The synthetic polypeptide consisting of a polypeptide represented by SEQ ID NO: 1 and a polypeptide represented by SEQ ID NO: 2 and the mixture of a polypeptide represented by SEQ ID NO: 1 and a polypeptide represented by SEQ ID NO: 3 can increase the expression of SOX-9 and collagen type II at arthritic sites and induce mobilization of mesenchymal stem cells that can differentiate into chondrocytes to promote differentiation of chondrocytes.

Furthermore, another aspect of the present invention relates to a method for preventing or treating arthritis, comprising the step of administering to a subject a pharmaceutical composition comprising a synthetic polypeptide consisting of a polypeptide represented by SEQ ID NO: 1 and a polypeptide represented by SEQ ID NO: 2 or a mixture of a polypeptide represented by SEQ ID NO: 1 and a polypeptide represented by SEQ ID NO: 3.

The subject preferably is a mammal including a human and may include, without limitation, any arthritis patients who have suffered from or are suffering from or are susceptible to arthritis. The polypeptide may be delivered in a pharmaceutically effective amount to the arthritic site of the subject and may preferably be in the form of an injection, but not limited thereto. Particularly, the injectable is preferably administered to a mammalian subject, more preferably administered intraarticularly to a human patient.

Still another aspect of the present invention relates to the use of a pharmaceutical composition for the manufacture of a preventive or therapeutic agent for arthritis, comprising a synthetic polypeptide consisting of a polypeptide represented by SEQ ID NO: 1 and a polypeptide represented by SEQ ID NO: 2 or a mixture of a polypeptide represented by SEQ ID NO: 1 and a polypeptide represented by SEQ ID NO: 3.

Hereinafter, preferred Preparation Examples and Examples will be provided to facilitate understanding of the present invention. However, the following Preparation Examples and Examples are provided only for the purpose of better understanding of the present invention, and the present invention is not limited by the Preparation Examples and Preparation.

Preparation Example 1: Preparation of Polypeptide (KLD12-SP)

For the preparation of polypeptides having a therapeutic effect on degenerative arthritis, a polypeptide was prepared in which self-assembling polypeptide KLD12 represented by SEQ ID NO: 1 and substance P represented by SEQ ID No: 2 are bound, and was named "KLD12-SP". More specifically, KLD12-SP was synthesized by a solid-phase synthesis method as follows.

0.06 mmol of glutamic acid-Wang resin was placed in a standard reaction vessel, and the Fmoc of the resin was removed with base (20% piperidine). The Fmoc-amino acid was added to the carboxy terminus of the peptide to be synthesized, mixed with 1-hydroxybenzotriazole (HOBt) and diisopropylcarbodiimide (DIC), and activated to start synthesis. Subsequently, the peptide having the desired amino acid sequence was synthesized using the same method, and after coupling, the peptide was washed several times with N-methylpyrrolidone and dichloromethane and then dried. The resulting peptide was reacted with a 82.5:5:5:5:2.5 (v/v) solution of trifluoroacetic acid, phenol, thioanisole, water, and ethanediol for 2-3 hours to remove the protecting group, and the peptide was separated from the resin. To the solution was added cold ethyl ether to obtain a white precipitated peptide. The resulting peptide was purified by high performance liquid chromatography (HPLC) on a C4 semi-preparative column (Phenomenex). The column was equilibrated with buffer A containing water and 0.1% TFA, and the peptide was eluted with buffer B containing acetonitrile and 0.1% TFA to prepare KLD12 and KLD12-SP in which substance P was bound to KLD12, respectively. Information on the sequences used and synthesized in this Preparation Example is shown in Table 1 below.

TABLE 1

|  | Sequence | Remarks |
| --- | --- | --- |
| SEQ ID NO: 1 | KLDLKLDL KLDL | KLD12, self-assembling peptide |
| SEQ ID NO: 2 | RPKPQQFF GLM | substance P (SP) |
| SEQ ID NO: 3 | KLDLKLDL KLDLRPKP QQFFGLM | KLD12-SP |

The resulting KLD12 and KLD12-SP were mixed to prepare a peptide gel. KLD12 and KLD12-SP were each dissolved in a 295 mM sucrose solution to prepare a 1% peptide solution, and the resulting peptide solution was mixed with PBS to prepare a 0.5% peptide gel. In order to determine the therapeutic effects of various KLD12-SP peptides, KLD12-SP peptide solutions at various concentrations were prepared by mixing KLD12 and KLD12-SP peptides at weight ratios of 200:7, 200:14, and 200:3.5. The KLD12-SP solutions mixed at these weight ratios were named KLD12-SP1, KLD12-SP2, and KLD12-SP0.5, respectively. Moreover, an experimental group in which mesenchymal stem cells (MSCs) were added to the peptide solution containing KLD12 and KLD12-SP at a weight ratio of 200:7 was named KLD12-SP-MSC, and a control group containing a physiological saline solution was used.

The therapeutic effects of the resulting KLD12-SP1, KLD12-SP2, KLD12-SP0.5, and KLD12-SP-MSC on degenerative arthritis were determined by the following Examples.

For degenerative arthritis rat models used to determine the therapeutic effect on degenerative arthritis, 9-week-old rats were purchased from "Orient Bio", transferred to the Samsung Biomedical Research Institute, and then quarantined for 1 week. After 5 weeks of feeding, the degenerative arthritis models were used at 15 weeks of age. The degenerative arthritis models were prepared by dissecting the skin and fascia inside the patella, pushing the patella to the outside of the knee to expose the joint cavity, and then removing the anterior cruciate ligament, medial collateral ligament and medial meniscus with scissors. Subsequently, the patella was repositioned and skin closure was performed.

Example 1: Behavioral Experiments

Behavioral experiments were performed by measuring the knee joint function of rats (Orient Bio). Behavioral experiments were performed by placing an ink pad on the entire bottom of a 30 cm×30 cm×30 cm acrylic box with white paper attached to four sides, allowing the rats to move freely for 30 minutes, and collecting the white paper. The knee joint function was determined by drawing a line on a 5 cm area from the bottom of four sheets of white paper and measuring the number of times the front paws were marked on the area over 5 cm. Before injection, the number of times the front paws were marked was measured, and after injecting each 200 µL of KLD12-SP1, KLD12-SP2, KLD12-SP0.5, and KLD12-SP-MSC prepared in Preparation Example 1 into the joint cavities of the degenerative arthritis rat models using a 1 mL syringe, the number of times the front paws were marked was measured after 2 weeks and 4 weeks. The results are shown in FIG. 1.

Figure 1A:
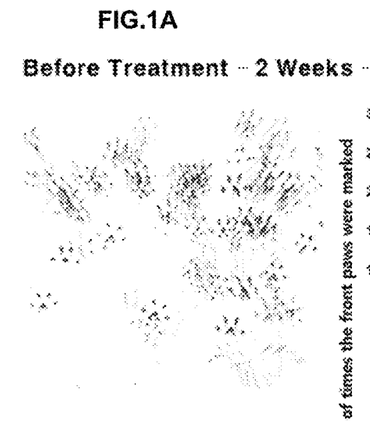
FIG. 1A is the appearance of rat front paws.
Figure 1B:
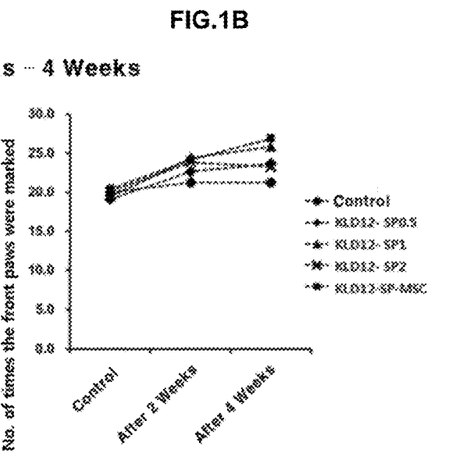
FIG. 1B is a chart that demonstrates the number of times the front paws were marked in control and treatment groups.

As shown in FIG. 1, the number of times was about 20 before treatment of KLD12-SP, but it was increased in the groups treated with KLD12-SP1, KLD12-SP2, KLD12-SP0.5, and KLD12-SP-MSC, from which it was determined that the knee joint function of the rats was improved, compared to the control group. In particular, KLD12-SP-MSC, in which stem cells and KLD12-SP were mixed, showed the most excellent improvement effect.

Example 2: Determination of Improved Bone Mineral Density Using Micro-CT

Patients with degenerative arthritis are at risk of osteoporosis and fractures due to reduced bone mineral density. Therefore, it was determined whether KLD12-SP, which can improve the knee joint function, could have the effect of improving bone mineral density. More specifically, each 200 μL of KLD12-SP1, KLD12-SP2, KLD12-SP0.5, and KLD12-SP-MSC was injected into the joint cavities of the degenerative arthritis rat models using a 1 mL syringe, and the knee joints were extracted after 4 weeks. After removal of muscles and fat tissues, the bone mineral density was measured on a Siemens Inveon Micro-PET/CT scanner. All tissues were scanned at intervals of 1.5 mm at 70 kV, 400 μA, and the rotation was set 0.5 degrees per step for 360 degrees to obtain scanned images. Each pixel had a resolution of 20.26 μm. Each scanned image was reconstructed using the Inveon Acquisition Workplace (IAW) software package (Siemens Medical Solutions, Knoxville, Tenn., USA) and analyzed with 2D and 3D image analysis software using the Inveon Research Workplace (IRW). The extracted knee joint was divided into four compartments such as medial femur (MFC), lateral femur (LFC), medial tibia (MTP), and lateral tibia (LTP), and the bone mineral density of each compartment was calculated in a region of interest (ROI) in the form of a cylinder at the front, center, and rear. Each ROI was 0.8 mm in diameter and 0.8 mm in length, and the ROI volume was approximately 0.45 mm$^3$. The bone mineral density of each compartment was calculated by comparing hounsfield units measured using a bar with known density (g/cm$^3$). The results are shown in FIG. 2.

Figure 2A:
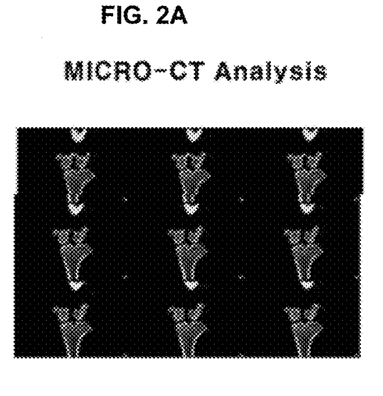
FIG. 2A is a picture of a Micro-CT scan of a rat knee joint.
Figure 2B:
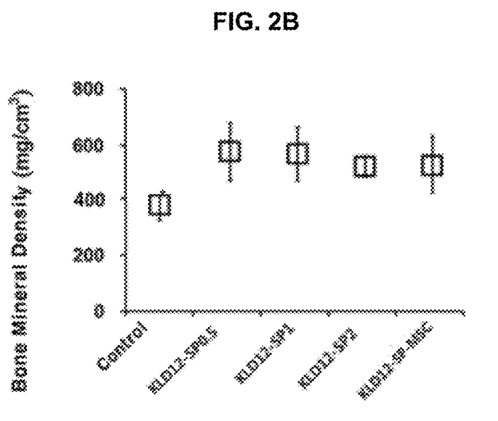
FIG. 2B is a chart of bone mineral density (mg/cm$^3$) of control and treatment groups.

As shown in FIG. 2, it was determined that the bone mineral density was increased in all KLD12-SP treatment groups, compared to the control group. The bone mineral densities of KLD12-SP1, KLD12-SP2, KLD12-SP0.5 and KLD12-SP-MSC were about 500 to 600 mg/cm$^3$, which were higher than that of the control group (about 400 mg/cm$^3$), indicating that KLD12-SP has an effect of improving bone mineral density at degenerative arthritic sites.

Example 3: Effect of KLD12-SP on Inhibition of Apoptosis

One of the pathogenic mechanisms of arthritis is apoptosis in articular chondrocytes, and it has been reported that apoptosis is increased in articular chondrocytes of arthritis patients. Therefore, it was determined whether KLD12-SP can inhibit degenerative changes due to aging by inhibiting the reduction of chondrocytes, rather than by inhibiting apoptosis in degenerative arthritis due to aging to promote regeneration of chondrocytes at the local sites.

In order to observe apoptosis at a single cell level in the arthritis rat models injected with KLD12-SP1 and KLD12-SP-MSC, terminal deoxynucleotidyl transferase mediated dUTP nick end labeling (TUNEL) staining was performed using a commercially available ApopTag Peroxidase In Situ Apoptosis Detection Kit (Cat No: S7100, Millipore). Tumor tissues with determined TUNEL expression were used as a positive control, and a negative control was reacted with a TUNEL reaction mixture without terminal transferase.

After 4 weeks from injection of KLD12-SP1 and KLD12-SP-MSC, the tissue slides obtained from the arthritis rat models and cut into 4-μm thick sections were left in a drying oven at 60° C. for 5 minutes, reacted with xylene for 5 minutes three times for deparaffinization, treated with 100%, 95%, 90%, 70% alcohol, and washed with distilled water. The tissue slides were pretreated with 20 μg/mL of proteinase K for 15 minutes, washed with PBS buffer containing Tween 20, reacted with a 3% $H_2O_2$ solution for 10 min to inhibit the activity of endogenous peroxidase, and then washed with PBS. The tissue slides were pre-incubated in a TdT reaction buffer for 10 minutes, and the TdT reaction mixture was seeded, reacted at 37° C. for 1 hour, immersed in a stop/wash buffer, stirred for 15 seconds, and then left at room temperature for 10 minutes to stop the reaction of the TdT reaction mixture. At this time, a humidified chamber was used to prevent drying of the tissues. After washing with PBS, the tissue slides were treated with HRP-conjugated anti-digoxigenin at room temperature for 30 minutes and then washed with water. The tissue slides were incubated at room temperature for 3 minutes using DAB as a coloring agent, and counterstained with Mayer's hematoxylin, followed by microscopic examination to observe brown-stained apoptosis. The results are shown in FIG. 3.

Figure 3A:
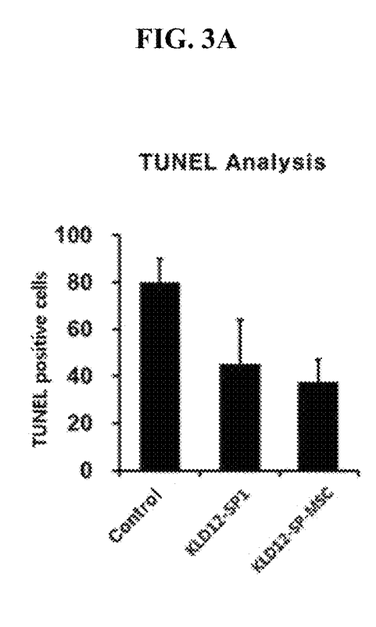
FIG. 3A is a bar chart of TUNEL Analysis of control and treatment groups.
Figure 3B:
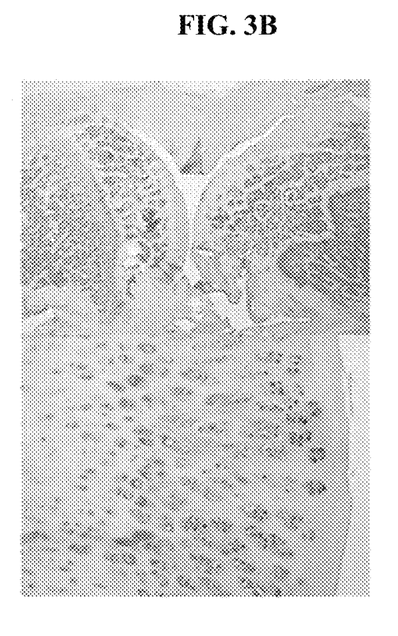
FIG. 3B is a picture of a microscopic slide examination of tissue.
Figure 4A:
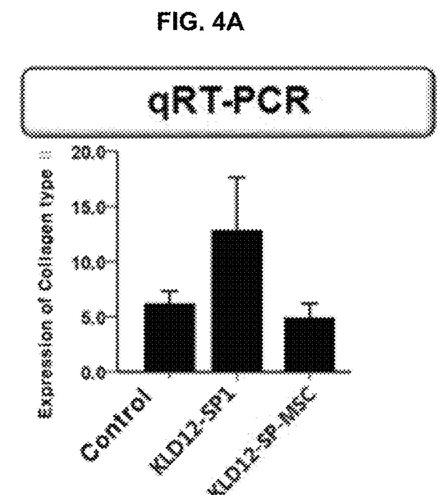
FIG. 4A is a bar chart of expression of collagen type II.
Figure 4B:
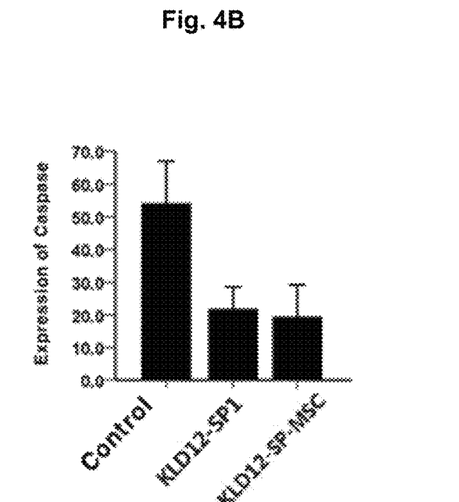
FIG. 4B is a bar chart of expression of Caspase.
Figure 4C:
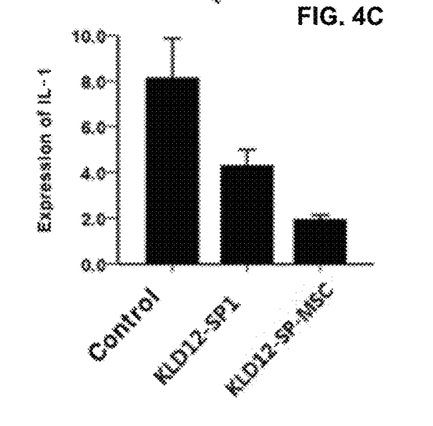
FIG. 4C is a bar chart of expression of IL-1.
Figure 4D:
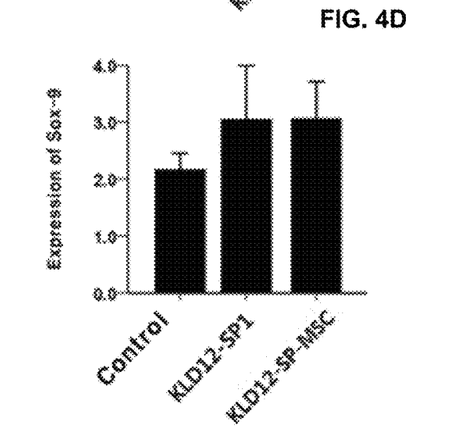
FIG. 4D is a bar chart of expression of Sox-9.

As shown in FIG. 3, it was determined that the apoptosis seen in brown was significantly reduced in the groups treated with KLD12-SP1 and KLD12-SP-MSC, compared to the control group. Therefore, it was determined that KLD12-SP has a preventive and therapeutic effect of inhibiting apoptosis due to arthritis as well as a regenerating effect in degenerative arthritis and thus can more effectively treat degenerative arthritis due to aging.

Example 4: Determination of RNA Expression Using Quantitative Real-Time PCR

Only cartilage was obtained from the knee joints of rats injected with KLD12-SP1 or KLD12-SP-MSC, and then finely chopped with scissors. The finely chopped cartilage pieces were dispersed in a 0.1% collagenase solution and shaken overnight at 37° C. Then, the cartilage pieces suspended in a solution were centrifuged, the supernatant was discarded, and the precipitates at the bottom were separated. The resulting precipitates were washed with PBS and filtered three times with a 100 μm filter to obtain chondrocytes. For quantitative RT-PCR, RNA was extracted from the resulting chondrocytes using an RNAi Mini Kit (QIAGEN, Hilden, Germany) according to the manufacturer's protocol. cDNA was synthesized from the extracted RNA using an Omniscript System Kit (QIAGEN) using an SYBR Green Master Mix (Applied Biosystems, USA) and amplified by polymerase chain reaction. The change in expression levels of collagen type II, SOX-9, IL-1β, and caspase-3 was determined using a 7500 RT-PCR system (Applied Biosystems). Primers used for quantitative RT-PCR are as follows. GAPDH was used as a housekeeping gene.

TABLE 2

|  | Forward | Reverse |
|---|---|---|
| Collagen Type II | CCCCTGCAGTA CATGCGG (SEQ ID. NO. 4) | CTCGACGTCAT GCTGTCTCAAG (SEQ ID. NO. 5) |
| SOX-9 | CTGAAGGGCTA CGACTGGAC (SEQ ID. NO. 6) | TACTGGTCTGC CAGCTTCCT (SEQ ID. NO. 7) |
| IL-1 | CACCTCTCAAG CAGAGCACAG; (SEQ ID. NO. 8) | GGGTTCCATGG TGAAGTCAAC (SEQ ID. NO. 9) |
| Caspase-3 | AATTCAAGGGA CGGGTCATG (SEQ ID. NO. 10) | GCTTGTGCGCG TACAGTTTC (SEQ ID. NO. 11) |
| GAPDH | GACATGCCGCC TGGAGAAAC (SEQ ID. NO. 12) | AGCCCAGGATG CCCTTTAGT (SEQ ID. NO. 13) |

The results are shown in FIG. 4.

As shown in FIG. 4, the expression of collagen type II, which is a major component of the extracellular matrix (ECM) of vitreous cartilage, was increased more than two times in rats injected with KLD12-SP1, and the expression of SOX-9, which is a gene involved in the proliferation and differentiation control of chondrocytes, was also significantly increased in all rats injected with KLD12-SP1 and KLD12-SP-MSC, respectively. On the contrary, the expression of IL-1β and caspase-3, which are inflammatory factors, was decreased to less than half of the control group in both rat groups injected with KLD12-SP1 and KLD12-SP-MSC. These results indicate that KLD12-SP has an excellent effect of inhibiting the activation of inflammatory response by effectively increasing the expression of factors involved in cartilage differentiation in degenerative arthritis and, at the same time, reducing the expression of inflammatory factors Example 5: Histological Analysis and Immunofluorescence Analysis The knee joints of rats with induced arthritis were extracted and histologically analyzed. The collected samples were fixed in a 10% (v/v) formalin solution and decalcified in a hydrogen chloride ethylene-diaminetetraacetic acid solution. The decalcified samples were embedded in paraffin, cut into 6-μm thick sections along the sagittal plane using a microtome. Then, the sections were stained with hematoxylin and eosin (H&E) for morphological analysis of cells, and also stained with Masson Trichrome (MT) and Alcian blue to evaluate the formation of cartilaginous tissue. Moreover, immunofluorescent staining was performed using collagen type II antibody (Chemicon, Darmstadt, Germany), caspase-8 antibody (Santa Cruz Biotechnology, Dallas, Tex., USA), and TIMP-1 antibody (Santa Cruz Biotechnology). Alexa Fluor 488 goat anti-mouse IgG (Invitrogen, Eugene, Oreg.), Alexa Fluor 594 donkey anti-rabbit IgG (Invitrogen), and Alexa Fluor 594 rabbit anti-mouse IgG (Invitrogen) were used as secondary antibodies. The tissue samples were counterstained with DAPI (4',6-amidino-2-phenylindole; Molecular Probes) for observation of cell nuclei, and the stained tissue samples were examined under a fluorescence microscope (Eclipse TE2000U, Nikon, Tokyo, Japan), photographed from 4 randomly selected areas, and quantified using the imageJ program.

Moreover, in order to determine whether substance P bound to the self-assembling polypeptide was retained in the knee joints of rats, the samples were stained with substance P antibody (Santa Cruz Biotechnology), and Alexa Fluor 488 chicken anti-goat IgG (Invitrogen) was used as a secondary antibody. The stained samples were examined under a fluorescence microscope (Eclipse TE2000U) at 200× magnification and photographed from 4 randomly selected areas. Then, the images with specific expressions were processed using the imageJ program and then quantified.

Figure 5A:
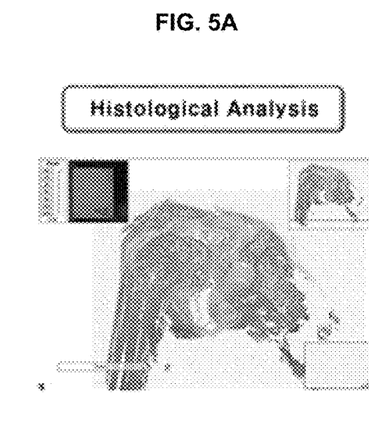
FIG. 5A shows a histological analysis of knee joints of rats.
Figure 5B:
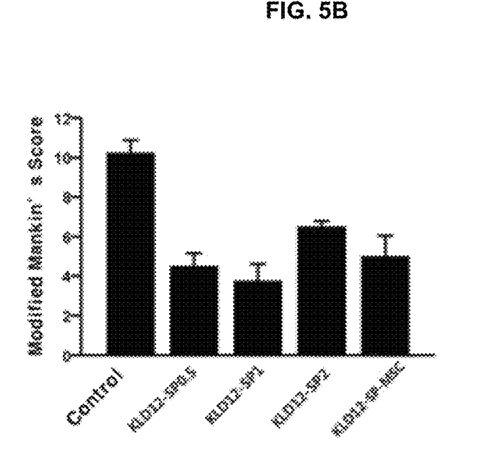
FIG. 5B is a bar chart of Modified Mankin's Score in control and treatment groups of rats.
Figure 6:
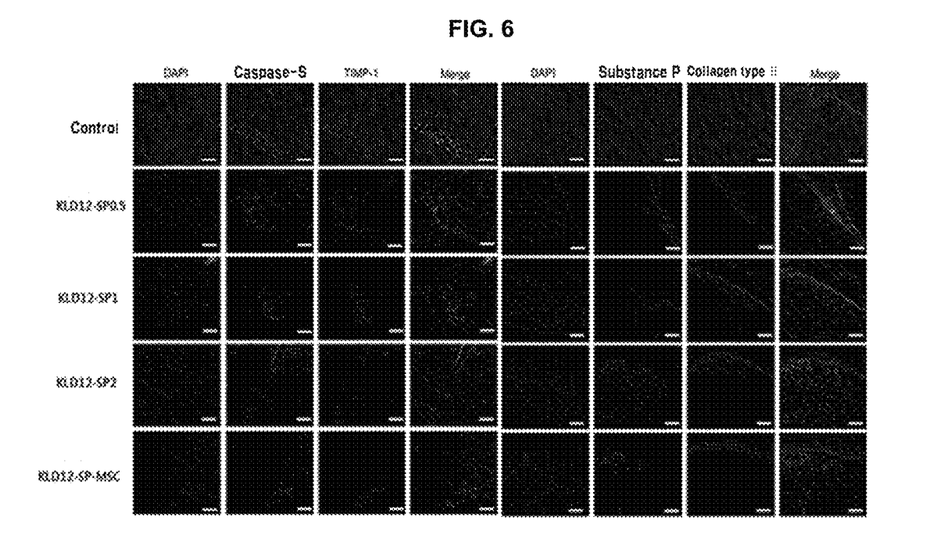
FIG. 6 is a panel of immunofluorescent images of expression of various proteins in knee joints of control and treatment groups of rats.

The results are shown in FIGS. 5 to 7.

As shown in FIG. 5, the histological analysis showed that Mankin's scores indicative of the degree of damaged cartilaginous tissue in arthritis rat models injected with KLD12-SP1, KLD12-SP2, KLD12-SP0.5 and KLD12-SP-MSC were lower than that of the control groups. Mankin's score is indicative of normal tissue when it is closer to 0, and the lowest score was observed in the KLD12-SP1 group. These results indicate that all KLD12-SP peptides effectively improve damaged cartilaginous tissues in arthritic rat models.

Figure 7A:
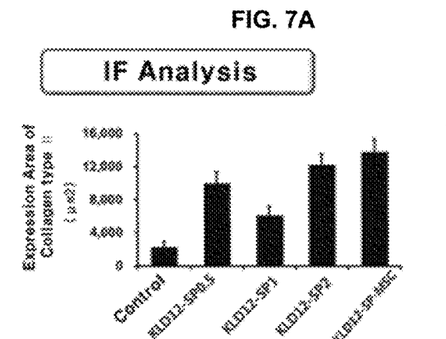
FIG. 7A is a bar chart of expression area of Collagen type II.
Figure 7B:
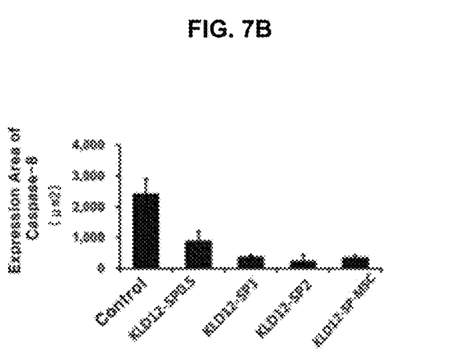
FIG. 7B is a bar chart of expression area of Caspase-8.
Figure 7C:
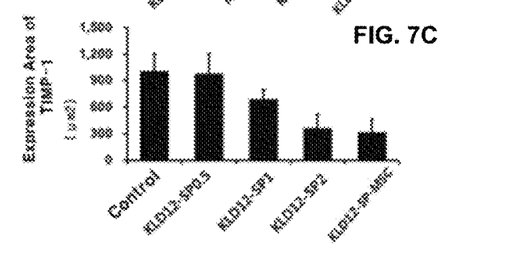

As shown in FIGS. 6 and 7, the expression of caspase-8 and TIMP-1 was reduced in arthritis rat models injected with KLD12-SP1, KLD12-SP2, KLD12-SP0.5 and KLD12-SP-MSC, compared to the control group, and the expression of collagen type II was significantly increased in all groups. It was also determined that substance P (SP) bound to KLD12 was retained in the knee joints of rats. More specifically, the expression of collagen type II was increased about twice in all experimental groups, compared to the control group, and the expression of caspase-8 and TIMP-1 showed a tendency to decrease depending on the content of substance p (SP) in the KLD12-SP treatment groups.

Example 6: Ability of KLD12-SP to Mobilize Stem Cells

Figure 8:
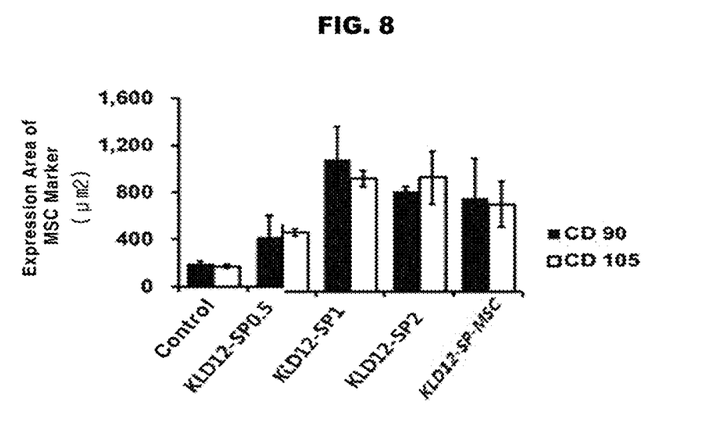
FIG. 8 shows increased expression of mesenchymal stem cell markers CD90 and CD105 by KLD12-SP treatment and their ability to mobilize stem cells.

Since substance P of KLD12-SP is expected to have the ability to mobilize mesenchymal stem cells, immunofluorescent staining was performed using CD90 (Thy-1 antibody, Santa Cruz Biotechnology) and CD105 (anti-endoglin monoclonal antibody, Millipore, Temecula, Calif.), which are markers specifically expressed in mesenchymal stem cells, in the groups treated with KLD12-SP-MSC and KLD12-SP without MSC. Alexa Fluor 594 donkey anti-rabbit IgG (Invitrogen) and Alexa Fluor 488 goat anti-mouse IgG (Invitrogen) were used as secondary antibodies and counterstained with DAPI to observe cell nuclei. The results are shown in Fig.

As shown in FIG. 8, the expression of CD90 and CD105, which are mesenchymal stem cell markers, was at least twice that of the control group in the group treated with KLD12-SP without MSC. These results indicate that KLD12-SP has the ability to mobilize mesenchymal stem cells to the arthritic sites, and it was determined that the regeneration of chondrocytes can be performed more actively by the mesenchymal stem cells migrating to the arthritic sites.

The invention claimed is:

1. A method for treating arthritis, comprising the step of administering to a subject a pharmaceutical composition comprising a mixture of a polypeptide represented by SEQ ID NO: 1 and a polypeptide represented by SEQ ID NO: 3.

2. The method for treating arthritis of claim 1, wherein the polypeptide represented by SEQ ID NO: 3 is a synthetic polypeptide consisting of a polypeptide represented by SEQ ID NO: 1 and a polypeptide represented by SEQ ID NO: 2, wherein the polypeptide represented by SEQ ID NO: 1 is a self-assembling polypeptide and wherein the polypeptide represented by SEQ ID NO: 2 is substance P.

3. The method for treating arthritis of claim 1, wherein the polypeptide represented by SEQ ID NO: 1 and the polypeptide represented by SEQ ID NO: 3 are mixed at a weight ratio of 200:1 to 200:200.

4. The method for treating arthritis of claim 1, wherein the arthritis is at least one selected from the group consisting of osteoarthritis, degenerative arthritis, osteochondritis dissecans, joint ligament damage, meniscus tear, infectious arthritis, psoriatic arthritis, ankylosing spondylitis, rheumatoid arthritis, and juvenile rheumatoid arthritis.

5. The method for treating arthritis of claim 4, wherein the degenerative arthritis is idiopathic degenerative arthritis or secondary degenerative arthritis.

6. The method for treating arthritis of claim 4, wherein the degenerative arthritis occurs in at least one site selected from the group consisting of a knee, a finger, a jaw, a hip, and a waist.

7. The method for treating arthritis of claim 1, wherein the synthetic polypeptide inhibits apoptosis of chondrocytes.

8. The method for treating arthritis of claim 1, wherein the synthetic polypeptide has anti-inflammatory activity and promotes regeneration of chondrocytes.

9. The method for treating arthritis of claim 1, wherein the mixture further comprising mesenchymal stem cells.

* * * * *